United States Patent [19]
Ichikawa et al.

[11] Patent Number: 4,617,941
[45] Date of Patent: Oct. 21, 1986

[54] BLOOD COLLECTOR

[75] Inventors: Toshiji Ichikawa, Chofu; Atsushi Shimizu, Tokyo, both of Japan

[73] Assignee: Terumo, Tokyo, Japan

[21] Appl. No.: 637,858

[22] Filed: Aug. 6, 1984

Related U.S. Application Data

[63] Continuation-in-part of Ser. No. 613,746, May 23, 1984, abandoned, which is a continuation of Ser. No. 370,921, Apr. 22, 1982, abandoned.

[30] Foreign Application Priority Data

May 20, 1981 [JP] Japan ................................. 56-76311

[51] Int. Cl.⁴ .............................................. A61B 5/14
[52] U.S. Cl. .................................... 128/765; 128/766
[58] Field of Search ............... 128/763, 764, 765, 766; 604/236, 273, 245, 246, 247, 248

[56] References Cited

U.S. PATENT DOCUMENTS

| | | |
|---|---|---|
| 3,960,139 | 6/1976 | Bailey . |
| 3,978,846 | 9/1976 | Bailey . |
| 4,133,304 | 1/1979 | Bailey . |
| 4,206,768 | 6/1980 | Bailey . |
| 4,340,067 | 7/1982 | Rattenborg . |
| 4,519,402 | 5/1985 | Andersen ............................ 128/765 |

FOREIGN PATENT DOCUMENTS

| | | |
|---|---|---|
| 0047176 | 3/1982 | European Pat. Off. . |
| 0047806 | 3/1982 | European Pat. Off. . |
| 52-42064 | 9/1977 | Japan . |
| 53-49268 | 11/1978 | Japan . |
| 366126 | 1/1963 | Switzerland . |

*Primary Examiner*—Edward M. Coven
*Attorney, Agent, or Firm*—Frishauf, Holtz, Goodman & Woodward

[57] ABSTRACT

A blood collector comprising a collection container in the form of a tube having a forward end adapted for drawing of blood into the container and an opened rear end, a closure unit adapted for closing the opened rear end of the collection container, and a mechanism including a valving element for allowing passage of air when blood is flowing into said container and preventing passage of air and blood when said container is filled with blood, said valving element of said mechanism including an air passage and a filter member communicating with the air passage, said filter member comprising water insoluble but water-swellable polymeric material and provided at least at the contact portion of the closure member with collected blood. Air contained in the blood collecting space of the collection container is expelled through the valving element by the collected blood which rises to a desired level for expelling air from said space practically completely. As the blood contacts the water insoluble but water-swellable high polymeric material contained in filter member of the valving element, the material swells into gel body to block the air passage in the valving element connecting to outside of the collector. Thus blood analysis may be effected without influences by outside air and air otherwise contained in the blood collecting space.

9 Claims, 10 Drawing Figures

BLOOD COLLECTOR

CROSS-REFERENCE TO RELATED APPLICATIONS

This is a continuation-in-part of Ser. No. 613,746 filed May 23, 1984, abandoned which is a continuation of Ser. No. 370,921 filed Apr. 22, 1982, now abandoned.

BACKGROUND OF THE INVENTION

1. Field of the Invention

This invention relates to a blood collector with a mechanism for allowing passage of air and preventing passage of air and blood. More particularly, it relates to such blood collector with a mechanism for allowing passage of air and preventing passage of air and blood which is especially used for blood inspection called blood gas analysis, wherein air removal and sealing process may be effected reliably while the process is checked visually.

2. Description of the Prior Art

In order to grasp the state of acid base balance or the lung function of a human body, blood inspection called blood gas analysis is effected, with a view to measurement of oxygen or carbon dioxide contents in the arterial blood or of $p^H$ or oxygen saturation values of the artery, and to qualitative analysis of the electrolyte components in the blood, such as $HCO_3^-$, $Na^+$, $K^+$ and $Cl^-$.

In such blood gas analysis, measured results may be seriously affected by occasional mixture of air in the blood sample under examination. Therefore, it is of utmost importance to expel air from the collected blood sample.

To this end, a heparin solution is drawn as anticoagulant into the syringe of the collection container, prior to blood collection or the collection container is filled in advance with a heparin solution (see Japanese Utility Model Publication Nos. 49268/1978 or 42064/1977), to fill the dead space in the container or in the hypodermic needle with heparin solution.

The heparin solution used has the concentration generally in the order of 1000 units/ml, with water or physiological salt solution being used as diluent solvent. However, since this heparin solution is mixed with collected blood to dilute the blood, the results of blood gas analysis may be effected by fluctuations in the blood dilution degree by the heparin solution, resulting in accurate blood gas analysis.

It is therefore required to add heparin as an anticoagulant in a dried state into the syringe of the collection container to obviate the risk of blood dilution by the heparin solution, and to provide the blood collector with a separate mechanism for allowing air removal from the collector and sealing the collected blood from outside air. An example of such mechanism is described in the specification of U.S. Pat. No. 4,206,768.

According to said patent, the blood collector has an operating unit including a plunger and a gasket, said operating unit sliding in the collection vessel and closing the opened rear end of the container. The operating unit has a plastic thread or string which is inserted between the inner wall of the collection container and the outer wall of the gasket, whereby a gap connecting to outside is delimited in a portion of the rear inner end of the container. Air contained in the inside of the hypodermic needle and of the container is pushed up by the blood being collected and is discharged out of the container through the gap defined by the plastic string. After expulsion of air and completion of blood collection, the needle is removed from the blood vessel and the needle end is sealed as with rubber etc. The plunger is then rotated to take up the plastic string on the plunger. The rear end of the container may then be closed and sealed, with the gasket in intimate contact with the inner wall of the container. The blood collected may thus be sealed from outside air.

Such blood collector of the prior art has, however, certain defects in use and manufacture. Thus, in the case of a delay caused in extracting the hypodermic needle from the vein, the blood may leak out of the container by way of the string. Moreover, certain skill is required in blood collection because the pierced portion must be held with one hand while needle is removed from blood vessel and, in addition, plunger rotation as well as withdrawl of the collector must be made with one hand. Moreover, in manufacture of such blood collector, manual operation is required for attaching the plastic string between the gasket and the collector container. So the production en masse is a matter of considerable difficulties, because of painstaking labor involved in the manufacture, resulting in a rise in cost of the manufacturing process.

OBJECTS OF THE INVENTION

In view of the foregoing, a principal object of the present invention is to provide a blood collection device which directs a continuous blood flow from artery or vein with a mechanism for allowing passage of air and preventing passage of blood, wherein the possibility that the air originally contained in the collection container or be mixed into the collected blood may be positively excluded.

A second object of the present invention is to provide a blood collector with a mechanism for allowing passage of air and preventing passage of air and blood, wherein the gasket or stopper of the closure unit, formerly made of opaque rubber, is made of transparent material, and wherein a valving element is mounted in the transparent material, and wherein a valving element is mounted in the transparent molded body, in such a manner that the process that the blood introduced into the collection container gradually expels the air from the container and contacts the valving element to effect sealing from outside air following complete expulsion of air, may be checked visually.

A third object of the present invention is to provide a blood collector with a mechanism for allowing passage of air and preventing of air and blood, wherein when the gasket or stopper is formed as a transparent member, the latter is made of resilient material to facilitate assembly of the gasket or stopper to the collection container and for positive intimate contact of the gasket or stopper with the collection container.

A fourth object of the present invention is to provide a blood collector with a mechanism for allowing passage of air and blood, wherein when both the collection container and the closure unit are formed of transparent members, these members may be differentially tinted for possible distinction between the collection container and the closure unit and for checking of blood level relative to these components.

SUMMARY OF THE INVENTION

As a result of persevering research, the present inventors have found that the following arrangement is subservient to the realization of the above objects, and arrived at the present invention.

In brief, the present invention resides in a blood collector comprising a blood collection container in the form of a tube having its forward end adapted for drawing of blood therethrough into the blood collection container and having its rear end opened, a closure unit mounted to said collection container for closing the opened rear end of the container, and a mechanism for allowing passage of air and preventing passage of air and blood, said mechanism having a valving element mounted to at least that portion of the closure unit which may contact with collected blood said valving element providing communication between the inside and outside of said collection container and containing therein water-swellable polymeric material.

In case of collecting a predetermined amount of blood, the closure unit is a stopper fixedly mounted at a predetermined position in the collection container. In case of collecting varying amounts of blood, the closure unit is formed of a gasket slidable in the collection container and of a plunger for operating said gaseket.

Preferably, the forward end of that portion of the closure unit which encloses said valving element is formed as a skirt extending from the valving element housing portion towards its radially outer rim portion, said skirt having a gradually decreasing thickness in such direction and said rim portion sliding on the inner wall of the collection container in intimate contact therewith. The gasket or stopper enclosing the valving element is preferably formed as a transparent member which may preferably be made of resilient material such as rubber or elastomer as will be discussed below. When the gasket or stopper is formed as a transparent member it may be tinted for distinction from the similarly transparent outer collection container.

BRIEF DESCRIPTION OF THE DRAWINGS

FIG. 5b is a front view of the plunger shown in FIG. 5a.

DESCRIPTION OF THE PREFERRED EMBODIMENTS

Figure 1:
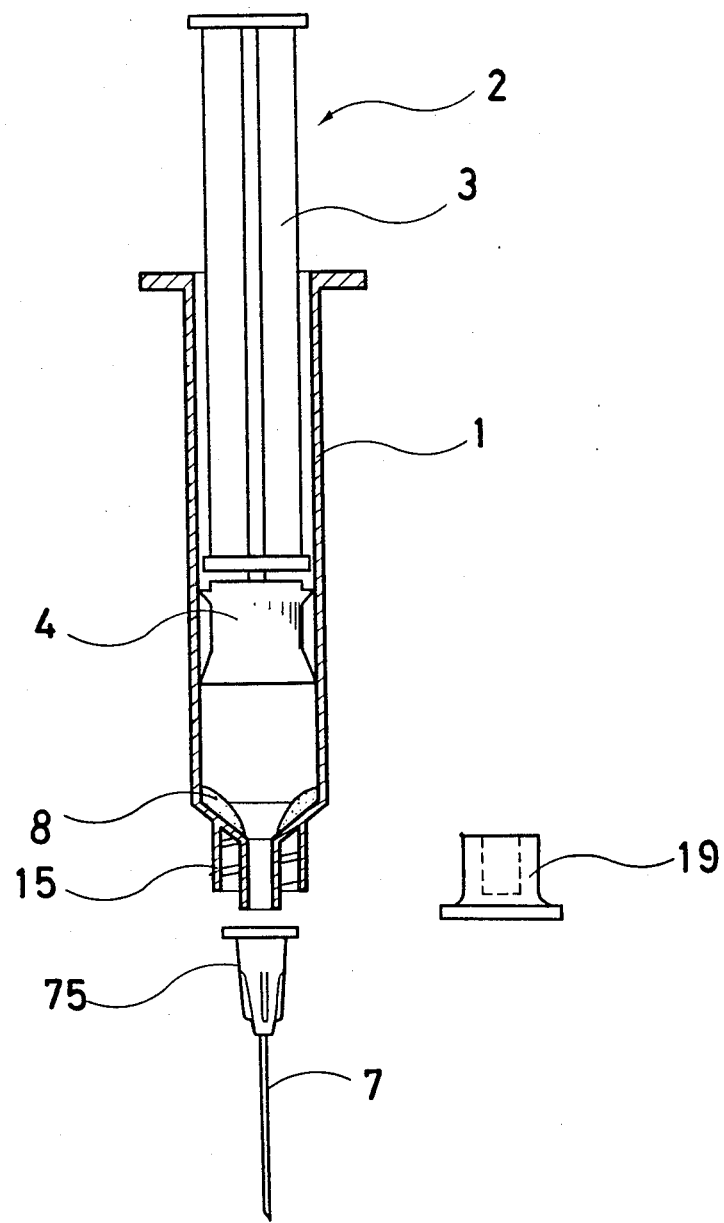
FIGS. 1, 2 and 3 are front views, shown partially in section, and showing various embodiments of the present invention.
Figure 2:
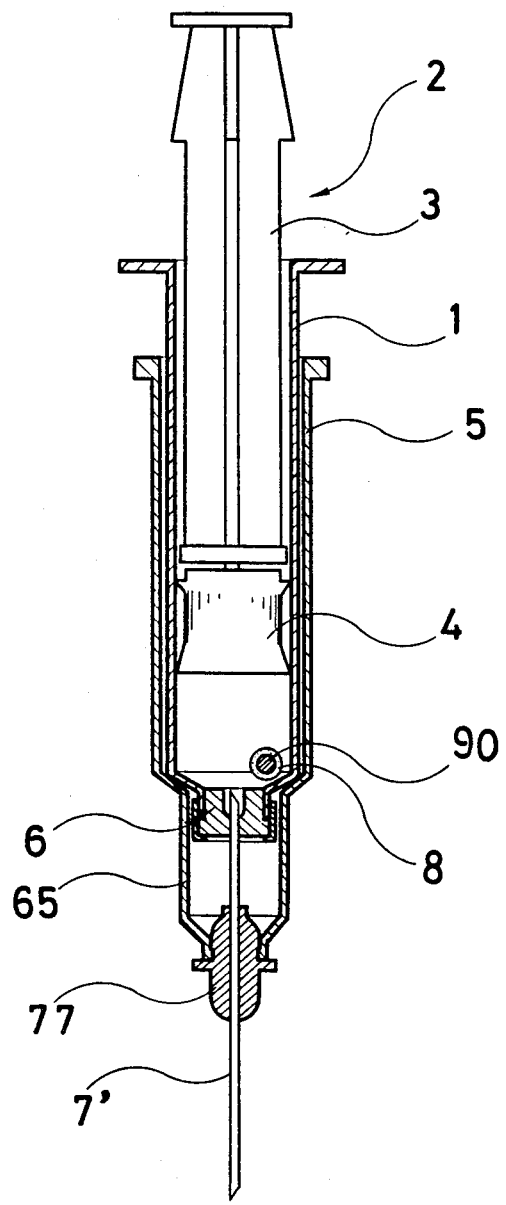
Figure 3:
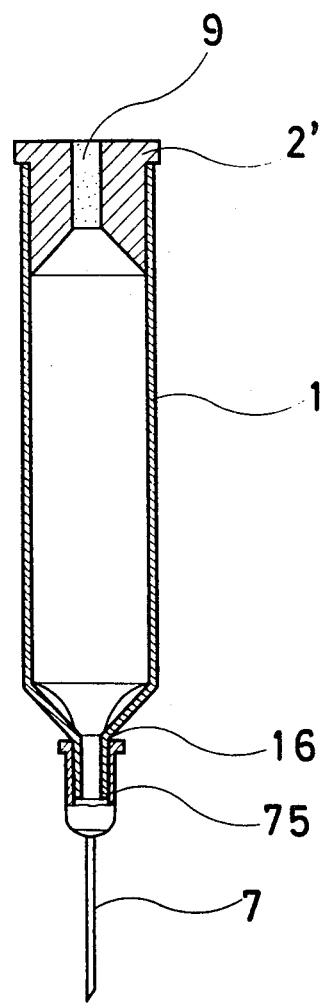

The blood collector with the mechanism allowing passage of air and preventing passage of blood according to the present invention has a collector container 1 in the form of a tube. As shown in FIGS. 1 to 3, the container 1 comprises a transparent tube of glass or plastic having a forward end adapted for drawing blood, and an opened rear end. A closure unit is inserted into the collector container 1. The closure unit is introduced into the tubular body for closing its opened rear end and may be constructed in one of the following two modes.

According to the first mode, the closure unit is designed as an operating unit 2 adapted to close the opened rear tube end and to be movable within the tube in tight sliding contact with the inner peripheral wall of the tubular body. In such a case, blood may be collected in varying amounts.

As for such operating unit 2, it is only necessary that a valving member to be described later may be mounted to the operating unit so that the inside of the collecting container made up of the forward end face of the unit 2 and the inner peripheral wall of the container 1 may communicate with the outside atmosphere towards the operating unit. Hence, an operating unit 2 of any desired shape or construction may be used provided that the above conditions are satisfied. However, the structure of the operating unit shown in FIGS. 1 and 2 wherein the head of a plunger 3 is operatively connected as by fitting same to the rear side of a columnar gasket 4 of resilient material abutting and slidable against the inner peripheral wall of the container 1, or the structure shown in FIG. 4 wherein the plunger 3 is fitted with resilient rings 4', 4', preferably O-rings, for connection to the inner wall of the container, said resilient rings abutting against the inner wall of the container 1 so as to allow for sliding of the plunger 3 along said inner wall, may be more preferred to a structure wherein the operating unit 2 simply consists of a plunger adapted for sliding in the tubular body.

According to a second mode, the closure member may be designed as a seal stopper 2' inserted and secured in a predetermined position in the collector container 1, as shown in FIG. 3. In such a case the stopper 2' is secured at such a position as to enable a predetermined amount of blood to be collected, and may be made of various materials, usually resilient material.

The forward end of the collector container 1 is designed to draw blood therethrough into the container. Therefore, the forward end of the container 1 need be constructed to allow for mounting thereto of a blood collecting hypodermic needle 7, or a heart catheter is fitted to such forward end as by the medium of a stop cock. The container 1 may have a forward end 16 in the shape of a Luer tip having a so-called Luer taper as shown in FIG. 3, and the hub 75 of the needle 7 or the rear catheter end may be mounted to the forward end 16 prior to blood collection. Alternatively, the forward end 15 of the container may be designed as Round Lock Luer tip wherein the hub 75 of the needle 7 or the rear catheter end may be threadably attached on the outer wall thereof to the threaded peripheral wall of the lure section and fittedly mounted on the inner wall thereof to said Luer section. On such occasions, the forward end 15 or 16 may preferably be kept in a sterilized state by a plug 19 of resilient material shown in FIG. 1.

Still alternatively, the needle 7 may be mounted to the container in advance as by fitting at the hub 75 by the medium of a Luer tip 16 provided to the end 16 of the container 1 as shown in FIG. 3, or of a Luer tip such as a Round-Lock Luer tip.

Still alternatively, the needle 7' may be threadedly mounted to a separate holder 5 as with hub 77, as shown in FIG. 2, the needle 7 piercing the forward end of the container 1 in a sealed state upon insertion of the collecting container 1 to the holder 5. In the example shown in FIG. 2, to the forward end of the collecting container 1 is fitted a plug 6 of rubber or similar resiient material that may be pierced by the rear end of the needle 7'. The vessel is completely sealed by a sealing member 65. Upon mounting the container 1 in position within the holder 5, the needle 7' pierces the plug 6 and proceeds into the inside of the collecting container 1. Upon removal of the container 1 from the holder 5 following the blood collection, the pierced hole in the plug 6 may be sealed completely due to the resiliency of the plug material.

In the arrangement of FIG. 2, the needle 7' may be replaced by a Luer adapter for a heart catheter having a rear piercing needle, said adapter being threadedly mounted to the holder 5 to complete the blood collector.

In accordance with the present invention, there is provided a valving member at least at the contact portion of the closure member with collected blood to allow for communication between the interior and exterior of the collecting container. Said valving member is made of water insoluble but water-swellable polymeric material in a dried state so as to be used as the mechanism allowing passage of air and preventing passage of collected blood.

Thus, the mechanism in accordance with the present invention for allowing passage of air and preventing passage of air and blood is contructed by a valving member provided to at least the contact zone of the operating unit 2 or stopper 2' with collected blood, said valving member containing water insoluble but water-swellable polymeric material, whereby at least a part of the rear end of the container 1 may be opened to the outside prior to blood collection and to contact of the valving member with collected blood. It may be appreciated that the operating unit 2 and the stopper 2' may be constructed in many different ways for providing the valving member at the rear end of the container 1 so as to allow for communication with the outside of at least a part of the operating member 2 or the stopper 2'.

First of all, the operating member 2 may be designed to collect the blood in different amounts.

Figure 4:
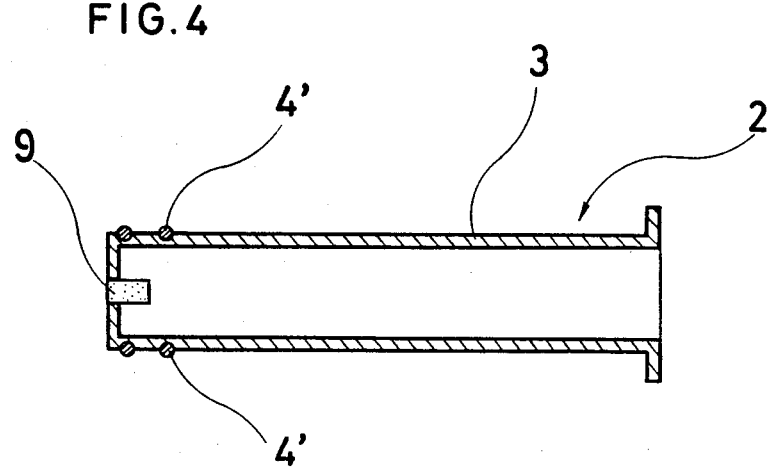
FIG. 4 is a sectional view showing the closure unit arranged as an operating unit in accordance with the present invention.

As typical of such structure, when resilient rings 4', preferably two O-rings, are fitted near the forward end of the plunger 3 to make up the operating member 2, as described above, that part of the forward end of the plunger 3 which is opposed to the outside and inside of the collecting container 1, may be formed by a valving member. Alternatively, as shown in FIG. 4, a valving member 9 may be mounted in a communication passage in the forward end of the plunger 3 connecting the inside and outside of the collection container.

When the operating unit 2 consists of the mutually connected plunger 3 and gasket 4, the forward end or head of the plunger 3 may be mounted as by fitting in an axial communication passage in the gasket 4, at leaset the forward end or the head of the plunger being then made as a valving member, or a valving member being annexed to the forward end the plunger. However, some difficulties may be experienced in mounting a rigid valving member to the forward end of the rigid plunger. Thereore, for providing a more simplified assembly, the valving member may be inserted and resiliently supported in an axial communication passage in the gasket.

Figure 5A:
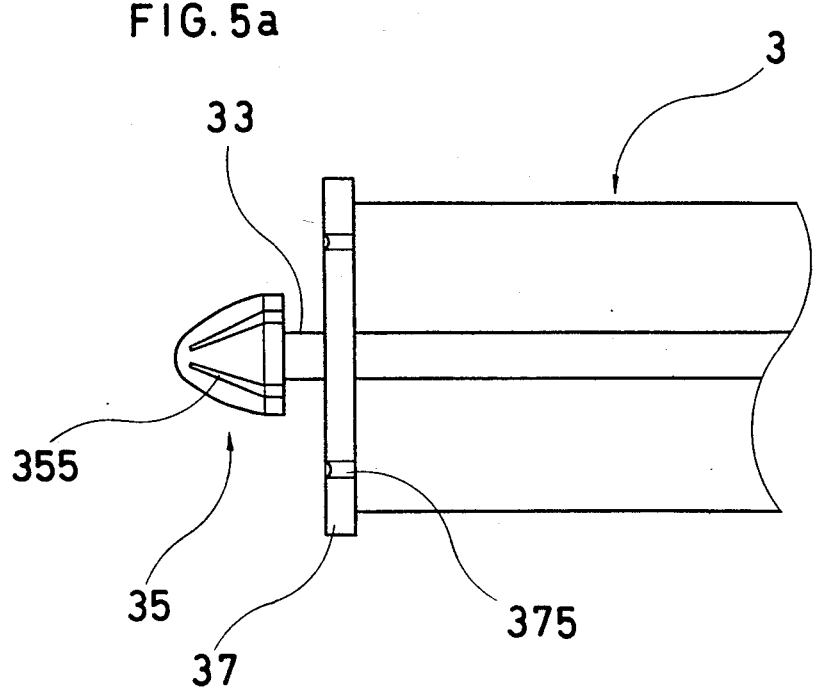
FIG. 5a is a partial side elevation of a plunger used when the closure unit is arranged as an operating unit, in accordance with the present invention.
Figure 5B:
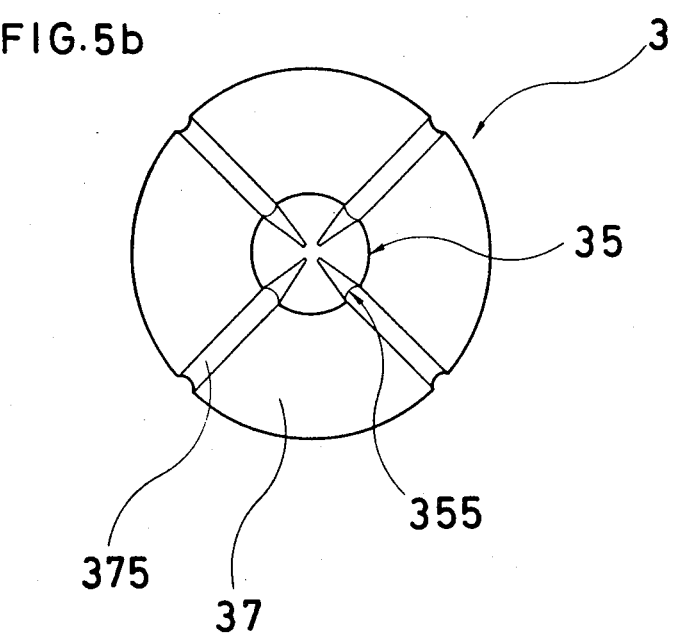

FIGS. 5a and 5b show an example of a plunger to be connected to a gasket according to the present invention, wherein FIG. 5a is a side elevation of the plunger and FIG. 5b is a front view of the cylinder head. The forward end or head 35 of the plunger 3 is adapted to fit with the rearward end of the gasket 4 and has on its surface a plurality of recesses 355 adapted to provide communication between a communication opening 43 in the gasket 4 and the outside of a blood collection container 1. In the example shown in FIG. 5a, the foremost part of the plunger 3 consists of an approximately conical foremost end 35, a neck 33 connected thereto and a flange portion 37 connected to neck 33. In such construction, the neck 33 may be of certain length to provide a gap between the rear end of the gasket and the flange portion 37 as shown in FIGS. 1 and 2. One or more cut-puts 375 may be formed in the flange portion 37 as shown in FIG. 5a. Although the plunger 3 is fitted to the gasket 4 in the present example, it is not limitative and the two members may be operatively connected to each other by any other means such as screws.

Figure 6:
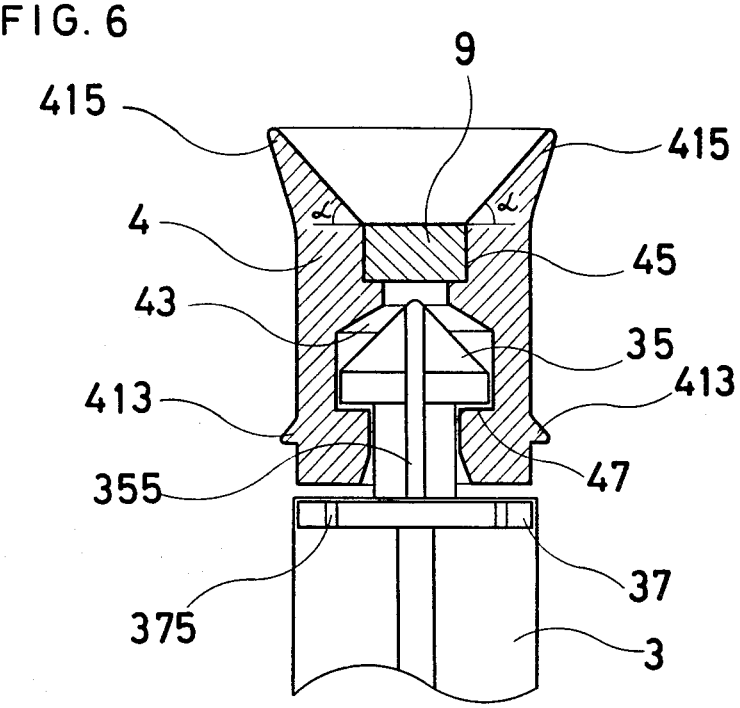
FIG. 6 is a side elevation, shown partly in section and showing a preferred gasket in accordance with the present invention.

The plunger such as shown in FIGS. 5a and 5b is shown to be mounted in FIG. 6 to a gasket 4 of the present invention. An axial communication passage 43 is provided in the center of the gasket 4. A recess 49 is formed in the forward central zone for communicating with the communication passage 43. A valving member 9 is inserted and supported in a housing 45 in the communication passage 43, said housing being disposed at the innermost end of the recess 49. Preferably, the inner surface of the recess 49 may be inclined at an angle α more than 45 degrees. Since the blood collevtor is used in general at an angle of 45 degrees from the vertical relative to the injection zone of a patients arm laid in horizontal position, air may be collected in the recess 49 and discharged when blood collection is made in such inclined position. Thus the possililily of air remaining in the container may be precluded almost completely.

The gasket 4 has the shape of a column having locally enlarged portions to facilitate sliding and prevent the gasket 4 from contacting with the container 1 in its entirety. The rearward end of the gasket has a rib 413 adapted for intimately contacting with and sliding on the collection container. Serious problems may arise when providing a rib 413 on the forward end of the gasket.

Figure 7:
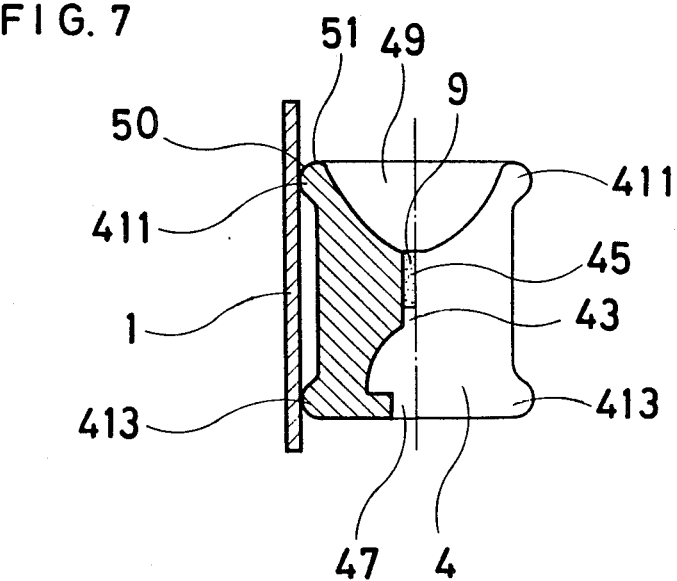
FIG. 7 is a side elevation, shown partly in section and showing the prior art gasket for illustrating certain problems inherent in the prior art gasket.

This is schematically shown in FIG. 7 and elucidated below. When the gasket 4 shown schematically in FIG. 7 is inserted into collection container 1 during assembly, the rib may be turned up or down as shown in the left half of FIG. 7 thus a deformed edge 51 being formed. Once the rib 411 has been thus deformed, there is produced a circumferential spacing 50 between the deformed edge 51 and the container 1. When the blood level rises during blood collection, the blood surface first contacts the deformed edge 51 of the rib 411, so that the air in the above spacing may be confined and caused to remain in the spacing. Thus the object of complete elimination of the air in the container for improving the analytical accuracy may not be realized. Even supposing that the rib 411 may not be deformed, it is not preferred to have the rib 411 so configured that the circumferential spacing described above be delimited between the rib 411 of the gasket 4 and the inner wall of the blood collection container 1. The shape of the rib 411 such as shown in FIG. 7 may cause such situation and therefore is not desirable.

In order that such circumferential spacing liable to trap air therein by blood may not be formed between the forward end of the gasket 4 and the container 1, the forward end of the gasket 4 is preferably shaped as shown in FIG. 6. The gasket 4 is operatively connected to the plunger 3 by fitting the head 35 of the plunger 3 into a housing 47, while the valving member 9 is mounted in the housing 45. Air in the collection container may be discharged to the atmosphere by way of recess 49, valving member 9, communication passage 43 and communication grooves 355 in the head 35 of the plunger 3. In addition, the ribs on the gasket 4, especially the forward rib 411, need be shaped to meet the above requirement. Thus the forward end of the gasket 4 is preferably shaped as a skirt 415 which is outwardly flared and has its thickness progressively decreasing towards its move or less pointed rim, starting from the mounting position of the valving member 9 at the center of the gasket 4. Thus, the forward end of the gasket is free of any portion liable to be deformed during assembly, thus eliminating any air sink 50 such as described above. It has been shown that blood collected may then act to discharge air from the collection container by way of the valving member 9, communication passage 43 and vent groove 60, there being no residual air in the container 1 or in the vicinity of the skirt 415 of the gasket 4, thus enabling an analysis with higher accuracy. As for the rib 413 at the rearward end of the gasket, special precautions need not be taken since the rib may be free of any problem such as may be encountered with the forward rib. It is apparent that, in the same way as the forward end of the gasket 4, the stopper 2' also must be designed so that air may not be confined in a similar manner.

The gasket 4 shown and described in connection with FIG. 6 and the stopper 2' shown and described in connection with FIG. 3 have the valving member 9 enclosed therein for excluding the air from the container 1 during blood collection and sealing the blood off from outside atmosphere at the required time, said valving member 9 containing water insoluble but water-swellable polymeric material. During blood collection, the level of blood collected in the container rises gradually. Simultaneously, the air in the container is passed to the outside through the valving element 9. When the container is completely, the blood contacts the valving element. The water-swellable component in the valving element 9 will then absorb water in the blood and be swollen into a gel body to seal the air passage that has so far existed in the element. Thus, there is no risk of the collected blood leaking to the outside or of the outside air contacting the collected blood. Such process may proceed at the gasket and the stopper.

It is to be noted that the gasket and the stopper are made of rubber in consideration of resiliency, dimensional stability, adhesiveness and moldability and therefore are usually opaque. Since the complete exclusion of air from the container and interruption from outside air occur at the opaque gasket or stopper, visual check or detection of the above process is simply based upon check of absence of blood leakage through the gasket or stopper. Thus, it is not possible to check that the air has been completely expulsed from the vessel or that the internal volume of the container has been completely interrupted from the outside. It is therefore preferred that such process be checked visually.

In view of this, in accordance with the present invention, the gasket or stopper used for enclosing the filter element containing water insoluble but water-swellable polymeric material and for excluding the air from the container and interrupting the outside air from collected blood; is made of transparent material. It may thus be possible to visually check the movement of blood, that is, the movement of air, through both the transparent collection container and the transparent gasket or stopper. The gasket and stopper need not be completely transparent, but may be translucent, it being only necessary that blood level may be ascertained from the outside.

Since the gasket or stopper is made transparent, it is preferred that the collection container may be visually distinguished from the gasket or stopper, inasmuch as it may become necessary later to pour the blood sample into plural test tubes for analysis, especially in case the collection container is designed to collect varying blood volume. Such visual distinction may be made by the following technique.

The transparent material of the gasket or stopper may be colored or not. In the latter case, the container and the gasket or stopper may preferably have different degrees of lightness or lucidity so that the two may be distinguished visually from each other. In general, since the collection container is white and transparent, the gasket or stopper may be colored for better distinction. However, in this case, the gasket or stopper tends to be lowered in transparency, so a denser color should be avoided.

The prior-art gasket or stopper has been made of opaque rubber which may not enable the operator to visually check the blood collection process until completion thereof described above. In view of this, the gasket or stopper in accordance with the present invention is made of transparent resilient material. The undermentioned materials are typical of such transparent resilient materials. The resilient material that may be used in accordance with the present invention is not limited to these materials used alone but may also be compounds of these materials with a variety of other elastomers.

Transparent elastomers
(1) Rubbery material—Transparent rubber, pure rubber, natural rubber.
(2) Thermoplastic elastomers—SBS elastomers, PVC elastomers, olefinic elastomers, silicon elastomers, EVA elastomers, polyurethane elastomers and polyester elastomers.

As a modification to the above, the gasket 4 in its entirety may be made as a valving element containing water insoluble but water-swellable polymeric material. In such case, the gasket 4 is not provided with the communication passage 43 designed for fitting a separate valving member. This modification has otherwise the identical structure with the above and therefore the illustration thereof in the drawing has been omitted. The gasket consisting of a valving element such as 9 containing water insoluble but water-swellable polymeric material usually has two ribs such as shown at 415, 413, and a housing such as shown at 47 towards rear for housing a plunger such as shown at 3. The forward portion of the gasket 4 is formard substantially flat and then a recess such as shown at 49 is provided in said forward portion. The risk that air may remain in the container may then be further reduced even when tilting the container for blood collection.

When the operating unit 2 consists of the plunger 3 and resilient rings 4', the rings 4' may be formed as a valving member 9 containing water insoluble but water-swellable polymeric material.

On the other hand, the closure unit may be formed as a stopper 2' which may be secured at a predetermined position in the tubular body to afford a predetermined amount of blood collection. In such case, the stopper 2' may be secured by engagement at the rear end of the tubular collection container 1, as shown in FIG. 3 or secured at any other position in the container by any suitable engaging or securing means.

The stopper 2' may be formed as a valving member containing water insoluble but water-swellable polymeric material. Alternatively the valving element may be inserted in an axial communication passage in the stopper 2', as shownn in FIG. 3. The stopper 2' may be made of opaque rubber or of transparent resilient material such as enumerated above. Similarly to housing the valving element 9 in the gasket 4, a recess may preferably be formed in the forward surface of the stopper 2' for communication with the communication passage, as shown in FIG. 3, and the valving element 9 placed in the innermost portion in the recess.

The valving element 9 discussed above may be made of a number of materials. As for moldability, a valving formed by baking a body of thermoplastic polymers such as polypropylene, polyethylene or polyacrylonitrile is most preferred. The valving elements 9 need be porous to allow passage of air. Preferably the element has a porosity in the range from 15 to 60 percent and preferably 20 to 40 percent, and the water insoluble but water-swellable polymeric material is contained in dried state. Preferably, the mean pore size may be 1 to 20 $\mu$m and most preferably be 5 to 10 $\mu$m.

The valving element 9 may generally be about 2 to 10 mm long, although no specific limitation is placed on the size of the element 9. The ratio of the valving element diameter to the tube inside diameter may generally be 0.1 to 1.0. The ratio of 1.0 represents that the gasket 4 or stopper 2' is formed in its entirety by a valving element.

The water insoluble but water-swellable polymeric material contained in the element 9 may preferably have a swelling degree such that the material may become swollen through absorption of water at ambient or room temperature to 100 to 1,000 times its own weight within 10 minutes upon contact with water.

A variety of materials known as highly water-absorbable resin may be used as such water-swellable polymeric material. Preferred materials that do not affect collected blood are starch-acrylonitrile, starch-acrylic acid, starch-acrylonitrile, starch-graft copolymer containing hydrolysate such as starch-sodium acrylate, partly saponified polyvinyl alcohol, acrylic polymers such as polyacrylates or acrylic acid-vinyl alcohol, polyethylene oxide or cellulosic polymers.

Such water insoluble but water-swellable polymeric materials are contained in dried state in the valving element, usually in the granular form. The contents of the water insoluble but water-swellable polymeric material may preferably be 1 to 60 and more preferably 10 to 40 wt. percent.

In general, the water insuluble but water-swellable polymeric material may be incorporated into the valving element by combining the material into the baked filter structure, that is, by homogeneously dispersing and mixing the water insoluble but water-swellable polymeric material into the above thermoplastic resin prior to molding, introducing the resulting mixture into a molding oven and applying heat and pressure thereto for molding.

In the above construction of the blood collector with a mechanism for allowing passage of air and preventing passage of blood, it is preferred that suitable anticoagulant 8 be contained in a dried state in the collection container 1. Heparin is preferred as an anticoagulant and may be contained in about 0.05 to 0.1 wt. percent related to the amount of blood collected. Heparin my be contained by having heparin 8 coated in a dried state on the inner wall of the collection container 1 as shown in FIGS. 1 and 3. Or alternatively, as shown in FIG. 2, heparin 8 may be coated on the surface of an agitator 90 consisting of a ball e.g. of stainless steel. Heparin may be coated by coating and subequent drying of a solution, especially an aqueous solution of heparin. Freeze drying is preferred after coating, that is, the coating may be frozen for sublimation of its water content. The agitator 90 may be effective to promote contact between blood and heparin by commotion of the collector after blood collection.

Experiment

Figure 8:
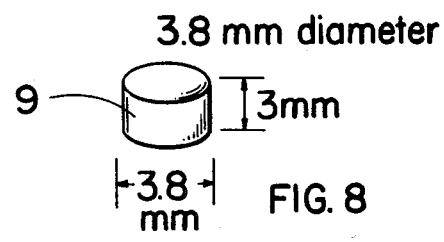
FIG. 8 is a perspective view of a preferred filter (valving member) 9 shown in FIG. 6.

A filter as shown at 9 in FIGS. 6 and 8 was mounted in a gasket. The filter was prepared by molding a mixture of 78% by weight of a polyethylene and 22% by weight of a starch-acrylonitrile graft copolymer both having an average particle size of 200 $\mu$m and sintering the molded part. The sintered filter was commercially available in the form of a rod of 3.8 mm diameter and 300 mm length from Spacy Chemical K.K. (Hachioji, Tokyo, Japan) under the trade name SGP Filter. The resultant sintered filter was porous and had an average pore diameter of 5 $\mu$m, a porosity of 40%, a thickness of 3 mm, and a diameter of 3.8 mm.

Figure 9:
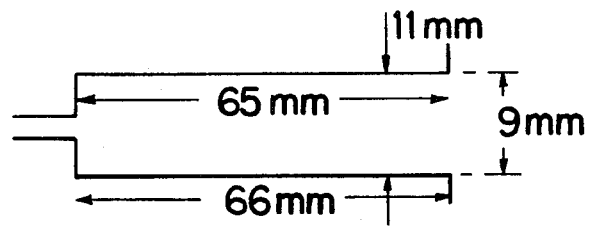
FIG. 9 shows a schematic representation of a syringe barrel of typical dimensions.

A syringe barrel (shown schematically in FIG. 9) used had an outer length of 66 mm, a inner length of 65 mm, an outer diameter of 11 mm, and an inner diameter of 9 mm and thus a spacial cross-sectional larea of 0.64 $cm^2$.

Blood was drawn in the blood collection space defined between the barrel and the plunger.

The plunger 3 was forced toward the barrel forward end by a force of 2 kg to apply a positive pressure of 3.14 $kg/cm^2$ to the blood. Leakage of blood was not observed under these conditions. Under higher positive pressures, observation became difficult because of leakage along the outer periphery of the gasket.

The plunger was pulled back toward the barrel rear end by a force of 0.8 kg to apply a negative pressure of 1.26 $kg/cm^2$ to the blood. Air entry into the blood collection space was not observed under these conditions. Under higher negative pressures, the plunger was withdrawn from the barrel.

In another run, the plunger was pulled back toward the barrel rrear end by a force of 0.7 kg to apply a negative pressure of 1.1 $kg/cm^2$ to the blood. Air entry was not observed.

Below is a Table showing the general and preferred ranges of "positive pressure" applied to the blood by the plunger being forced forward toward the barrel (see above Experiment) and "negative pressure" applied to the blood by the plunger being pulled back toward the rear end of the barrel (see above Experiment).

|  | General Range | Preferred Range |
|---|---|---|
| Positive pressure | 0.8–3.1 | 1.0–3.1 kg/cm$^2$ |
| Negative pressure | 0.3–1.3 | 0.5–1.3 kg/cm$^2$ |

OPERATION

The inventive blood collector with the mechanism allowing passage of air and preventing passage of air and blood, may be used as follows for blood collection.

A hypodermic needle 7 and the holder 5 are mounted in position, as the occasion may demand. When the operating unit 2 is used as closure unit, the unit 2 is set to a position to collect a predetermined amount of blood. The needle is then inserted into the artery so that the blood flows into the container 1 by way of the needle 7. Air contained in the needle 7, 7' and in the collection container 1 is expelled from the container 1 through the open pores in the valving element 9. When the blood has expelled all the air and contacted the valving element 9, the water insoluble but water-swellable polymeric material in the valving member 9 is swollen instantaneously to block the open pores in the member 9. When the gasket or stopper is made of transparent material, the process of air expulsion by the blood may be checked visually. Sealing from outside air of the collected blood following complete expulsion of air may also be checked visually whilst the container tilt is adjusted as required for complete air expulsion out of the container.

The needle 7 is then withdrawn out of the artery, without the risk of blood spilling from the needle point or seeping out through the valving member 9. Blood collection may be completed by having the needle point sealed with rubber or, when the holder 5 is used, by extracting the container 1 out of the holder. Reur tips or Reur adapters may be connected to the rear end of a heart catheter through a stop cock for blood collection from the heart catheter, as described above.

When desired to avoid contact with air during blood collection as far as possible, the needle 7 may be inserted into the artery, with the unit 2 pushed to avoid contact with air during blood collection as far as possible, the needle 7 may be inserted into the artery, with the unit 2 pushed to the forward end of the collection container. Once the collected blood has expelled the air in the container through the valving member, the unit 2 is caused to slide under arterial pressure spontaneously. The needle is withdrawn after the unit 2 has been pushed up to collect the blood in a predetermined amount. The open pores in the valving member 9 may also be blocked in this manner to effect aerophobic blood collection.

In the case of using the stopper 2' as a closure unit, the stopper 2, is preset for collecting a predetermined amount of blood in the collection container. Upon insertion of the needle into a blood vein or connection thereof to a heart catheter as described above, air expulsion and blockage of the valving pores will take place simultaneously with blood influx as described above. Provided that the stopper 2' is not opaque but made of resilient transparent material, the process of air expulsion by the blood may be checked visually, while container tilt may also be adjusted as required for complete air expulsion from the container. Interruption from outside air of collected blood upon complete air expulsion may also be checked visually.

EFFECTS OF THE INVENTION

According to the present invention, air contained in the collection container or in the needle may be prevented from mixing into collected blood, even in cases that heparin is enclosed in dried state in the blood collection container. In such a case, only by setting the unit 2 at a predetermined position, removal of air from the container and blocking the collected blood from the outside air may be effected positively and automatically. The collector may have improved reliability especially if the gasket or stopper is made of transparent material, since air removal and interruption may be checked visually. Thus, blood collection may be facilitated as compared to the case of using the conventional device, as a result, an accurate gas analysis may be assured through prevention of blood dilution by the heparin solution.

The effect proper to the present invention may be demonstrated by simply mounting a filter member at the contact portion of the closure unit with collected blood, said valving element containing water insoluble but water-swellable polymeric material so as to normally allow for communication between the inside and outside of the container 1.

Such valving member may be mounted according to various mounting modes in connection with the structure of the collection device. The overall device and monufacture thereof may be simplified by having the valving element inserted into the gasket 4 or stopper 2' or by having the gasket 4 or stopper 2' constructed as valving element. Further by providing a recess in the forward surface of the gasket, the risk of air remaining in the container in case of tilting the collector for blood collection may be eliminated. In addition, by having the valving member mounted in the gasket or stopper molded from transparent resilient material, it is possible to visually check the process of complete air removal from the container by the collected blood and interruption by the valving member of the collected blood from outside subsequent to air removal. Thus, the operational reliability in the blood collection may be improved over the case of using an opaque valving member made of rubber. Manufacture of the valving member may be facilitated by baking the body of valving material.

Such valving member may be supported by its own resiliency in the stopper or gasket made of resilient material.

The forward end of the gasket or stopper is formed as a skirt extending from the valving member housing towards a radially outer rim with the thickness of the skirt being gradually reduced in this direction. Thus, there is no spacing left between the forward end of the gasket or stopper and the container so that air may be expelled completely from the container by the collected blood.

The following is one of a variety of experiments conducted by the present inventors for ascertaining the effect of the inventive blood collector.

Experimental Example

The collection device shown in FIG. 1 was prepared for ascertaining the effect of the invention. The gasket 4 was of the structure shown in FIG. 6.

More in detail, the valving member 9 is a calcined filter made of polyethylene, having a porosity of 40 percent and a mean pore diameter of 5 μm. The calcined filter was cylindrical with an outside diameter of 4 mm and a height of 3 mm. Acrylic polymer ("Aquakeep" 10 SH, manufactured by Seitetsu Kagaku Kogyo KK of Japan) was used as water insoluble but water-swellable polymeric material, which was calcined as a blend with polyethylene for incorporating 20 wt. percent of the material in dried state into the calcined filter. The water-swellable polymeric material had a degree of swelling such that it may be swollen by water to 400 times its own weight at ambient temperature.

Such valving element 9 was introduced into gasket 4 as shown in FIG. 6. The gasket 4 was made of styrene butadiene rubber (SBR) with a diameter of 13.4 mm.

The gasket 4 was then fitted to the plunger 3 as shown in FIGS. 5a and 5b for providing a blood collector as shown in FIG. 1. In this constructional example, the container 1 was a plastic syringe with 5 ml capacity and the blood collection needle was a 22 G needle. 2 mg of heparin was coated on the inner wall of the syringe tube and dried in situ. With such collector, the space remaining e.g. in the inside of the needle when the unit 2 has been pushed to its lowermost position was 150 μl.

By using such collector, arterial blood was directly collected from the rabbit's carotis. The gasket 4 was set to a predetermined position and blood samples 1 ml, 2 ml and 3 ml were collected from each of two rabbits.

Blood collection was completed in half a minute to one and a half minute. After the predetermined amount of blood was collected, the needle was withdrawn from the artery or vein and the needle point was sealed with rubber tip. At this time, no blood seeped from the valving element.

Next, the values for $P^H$, $PO_2$ and $PCO_2$ were measured for each blood sample with the aid of a blood gas analyzer BMS-MK2 manufactured by Radiometer Co., Ltd. The results are shown in the following Table 1.

A blood collector having an identical structure with the one shown above except that the valving element is not fitted in the gasket 4 and the communication passage 43 is not provided in the gasket 4, was prepared for comparison sake. The collector was charged with a heparin solution of 1,000 units/ml, instead of with dried heparin.

The operating unit 2 was pushed down to fill the dead space with a residual heparin solution of 150 μl. Blood samples of 1 ml, 2 ml and 3 ml were collected from two rabbits under examination and the values for $P^H$, $PO_2$ and $PCO_2$ were measured. The results are likewise shown in the following Table 1.

| sample No. | item | collector | collected amounts (ml) | | |
|---|---|---|---|---|---|
| | | | 1 | 2 | 3 |
| 1 | PH | comparative | 7.36 | 7.36 | 7.36 |
| | | inventive | 7.36 | 7.36 | 7.36 |
| | PO₂ | comparative | 88.6 | 86.3 | 84.5 |
| | | inventive | 82.9 | 83.0 | 82.8 |
| | PCO₂ | comparative | 35.0 | 35.9 | 36.3 |
| | | inventive | 37.7 | 37.9 | 37.9 |
| 2 | PH | comparative | 7.35 | 7.35 | 7.35 |
| | | inventive | 7.35 | 7.35 | 7.35 |
| | PO₂ | Comparative | 93.8 | 90.5 | 91.0 |
| | | inventive | 87.7 | 87.3 | 87.8 |
| | PCO₂ | comparative | 31.0 | 31.9 | 32.3 |
| | | inventive | 34.0 | 33.9 | 33.8 |
| 3 | PH | comparative | 7.358 | 7.357 | 7.357 |
| | | inventive | 7.357 | 7.357 | 7.356 |
| | PO₂ | comparative | 84.8 | 83.9 | 82.4 |
| | | inventive | 82.8 | 83.0 | 82.0 |
| | PCO₂ | comparative | 34.5 | 36.0 | 37.1 |
| | | inventive | 38.3 | 37.9 | 37.9 |
| 4 | PH | comparative | 7.345 | 7.347 | 7.345 |

-continued

| sample No. | item | collector | collected amounts (ml) | | |
|---|---|---|---|---|---|
| | | | 1 | 2 | 3 |
| | | inventive | 7.346 | 7.347 | 7.346 |
| | PO₂ | comparative | 90.4 | 89.4 | 88.8 |
| | | inventive | 87.7 | 87.0 | 88.6 |
| | PCO₂ | comparative | 30.5 | 32.2 | 33.0 |
| | | inventive | 34.2 | 33.9 | 33.7 |

It will be observed from Table 1 that especially the value of $PO_2$ and $PCO_2$ are fluctuated in the conventional comparative device with differing amounts of blood collected, whereas such fluctuations may be avoided with the inventive device, on account of the different degree of blood dilution by the heparin solution for different amounts of blood collection. and of elimination of the circular spacing between the foremost end of the gasket and the collection container.

Similar results were obtained in a similar experiment conducted with a blood collector in which the gasket 4 was formed in its entirety by said valving member. Also similar results were obtained with a collector identical with the above collector except that starch-acrylonitril graft copolymer SPG manufactured by Henkel AG, with the swelling degree being 1,000 times in ten minutes of its volume and a polyvinyl alcohol polymer CP' manufactured by Nippon Gosei Kagaku Co. Ltd. of Japan with the swelling degree being 200 times in ten minutes of its volume. Comparable results were obtained with the collectors shown in FIGS. 2 and 3.

Subsequently, a blood collector was prepared in which the gasket was made from other transparent resilient material. Thermoplastic SBS material Elastomer Creiton G, manufactured by Shell Corporation, was used as the resilient material. Various coloring agents were added to the resilient material for providing transparent gaskets, tinted and not tinted. As blood collector was used as untinted transparent collector in current use. Because both collection container and the gasket are transparent, the following contrivance was made for distinction.

(a) With the gasket of uncolored transparent material, tests were conducted by varying the lightness or lucidity for distinction. Clear distinction was possible by the difference in lucidity. It was observed however that the more the difference in lucidity the harder it becomes to clearly see the blood level.

(b) With the gasket of tinted transparent material, the gasket may be easily distinguished from the untinted transparent collection container. During rise of the blood level in the gasket, air expulsion caused by blood drawn into the container may be checked visually. Sealing of collected blood from outside air may also be checked by the valving member turning to red as in the case of (a) for the uncolored transparent material. Thus blood collection amy be made with greater reliability than in the case of opaque gasket.

It was also observed that the gasket with a lighter color lends itself to clearer distinction and more reliable checking of the blood level. Denser tint is not desirable because it becomes harder to ascertain the blood level.

Tests were also conducted with the stopper of FIG. 3 made of transparent materials as with the gasket. It was found out that similar results to those obtained with the gasket could be obtained in respect of transparency.

We claim:

1. A blood collector comprising:

a blood collection container in the form of a tubular body defining a blood collection space, said tubular body having a forward end adapted for drawing blood therethrough into said collection container and having an open rear end;

a closure unit movably mounted to said collection container for closing said rear end of said collection container and having a portion which contacts with blood collected in said collection container, said closure unit being adapted to apply a positive pressure of at least 3.1 kg/cm$^2$ to blood in said collection container when moved toward the tubular body forward end and a negative pressure of at least 1.3 kg/cm$^2$ to blood in said collection container when moved toward the tubular body rear end; and valve means coupled to at least that portion of the closure unit which contacts with blood collected in said collection container, said valve means including:

a passage for passing air from said blood collection space to the exterior of said collection container; and a filter cooperatively associated with said passage for allowing passage of air through said passage when blood is flowing into said collection container and for blocking said passage to both air and liquid so as to cut off communication of air and blood between said blood collection space and the exterior of said collection container when said collection container is filled with blood and said blood contacts said filter, said filter occupying the entire cross-section off at least part of said passage;

said filter comprising a sintered porous body of polyethylene having a starch-acrylonitrile graft copolymer incorporated therein, said polymeric material of said filter substantially instantaneously swelling upon contact with water of said blood to grow or expand in volume through absorption of the water content of said blood in contact therewith so as to block the pores of said sintered body to block passage of both air and blood through said filter to thereby seal off said passage and to prevent flow of both blood and air to and from said blood collection space through said passage, said sintered body providing a predetermined mechanical strength to said filter sufficient to withstand said positive and negative pressures applied by said closure unit, and said sintered body remaining substantially the same size even after said contact with said water of said blood and said swelling of said polymeric material; and said polymeric material of said filter being sufficiently swellable upon contact with said water of said blood for not only preventing blood leakage under a positive pressure of up to about 3.1 kg/cm$^2$ applied by said closur unit toward the tubular body forward end, but also preventing air entry into the blood collection space under a negative pressure of up to about 1.3 kg/cm$^2$ applied by said closure unit toward the tubular body rear end.

2. The blood collector of claim 1, wherein said polymeric material of said filter is sufficiently swellable upon contact with said water of said blood to block said passage to prevent said blood leakage under said positive pressure of from about 0.8 to about 3.1 kg/cm$^2$, and to prevent said air entry into said blood collection space under a negative pressure range of from about 0.3 to about 1.3 kg/cm$^2$.

3. The blood collector of claim 1, wherein said polymeric material of said filter is sufficiently swellable upon contact with said water of said blood to block said passage to prevent said blood leakage under said positive pressure of from about 1.0 to about 3.1 kg/cm$^2$, and to prevent said air entry into said blood collection space under a negative pressure range of from about 0.5 to about 1.3 kg/cm$^2$.

4. The blood collector of claim 1, wherein said polymeric material of said filter is sufficiently swellable upon contact with said water of said blood to block said passage to prevent said blood leakage under said positive pressure of about 3.1 kg/cm$^2$ and to prevent said air entry into said blood collection sapce under said negative pressure of about 1 kg/cm$^2$.

5. The blood collector of claim 1, wherein said polymeric material of said filter is sufficiently swellable upon contact with said water of said blood to block said passage to prevent said blood leakage under said positive pressure of about 3 kg/cm$^2$ and to prevent said air entry into said blood collection space under said negative pressure of about 1.3 kg/cm$^2$.

6. The blood collector of claim 1, wherein said polymeric material of said filter is sufficiently swellable upon contact with said water of said blood to block said passage to prevent said blood leakage under said positive pressure of about 3 kg/cm$^2$ and to prevent said air entry into said blood collection space under said negative pressure of about 1.1 kg/cm$^2$.

7. The blood collector of claim 1, wherein said closure unit comprises a plunger and a gasket, said gasket being operatively connected to said plunger for sliding in intimate contact on an inner wall of said tubular body of said blood collection container, and said passage of said valve means comprises an axial communication passage substantially in the center thereof, said filter being mounted in said axial passage.

8. The blood collector of claim 1, wherein said closure unit comprises a stopper having a hole extended therethrough and fixedly mounted at a desired position in said blood collection container, said hole comprising said passage of said valve means; and said filter being mounted in said hole.

9. The blood collector of claim 1, wherein said copolymer has a particle size of about 200 μm; and the resultant sintered filter has an average pore diameter of about 5 μm and a porosity of about 40%.

* * * * *

UNITED STATES PATENT AND TRADEMARK OFFICE
CERTIFICATE OF CORRECTION

PATENT NO. : 4,617,941
DATED : October 21, 1986
INVENTOR(S) : ICHIKAWA

Page 1 of 2

It is certified that error appears in the above-identified patent and that said Letters Patent is hereby corrected as shown below:

Title page, under heading "Assignee:" change "Terumo" to -- Terumo Corporation --

Column 3, line 26, "gaseket" should read -- gasket --

Column 5, line 61, "leaset" should read -- least --

Column 6, line 19, "cut-puts" should read -- cut-outs --

Column 6, line 34, "collevtor" should read -- collector --

Column 7, line 48, after "completely" insert -- devoid of air --

Column 8, line 64, "formard" should read -- forward --

Column 9, line 17, "shownn" should read -- shown in --

Column 9, line 64, "insuluble" should read -- insoluble --

Column 10, line 60, "rrear" should read -- rear --

Column 11, lines 37-38, "Reur" should read -- Luer -- (both occurrences)

Column 12, line 29, "monufacture" should read -- manufacture --

Column 15, line 33, (Claim 1), "off" should read -- of --

Column 15, line 59, (Claim 1), "closur" should read -- closure --

UNITED STATES PATENT AND TRADEMARK OFFICE
CERTIFICATE OF CORRECTION

PATENT NO. : 4,617,941
DATED : October 21, 1986
INVENTOR(S) : ICHIKAWA

It is certified that error appears in the above-identified patent and that said Letters Patent is hereby corrected as shown below:

Column 16, line 26, (Claim 4), "sapce" should read -- space --.

Signed and Sealed this

Tenth Day of May, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,617,941

DATED : October 21, 1986

INVENTOR(S) : Toshiji Ichikawa et al.

It is certified that error appears in the above-identified patent and that said Letters Patent is hereby corrected as shown below:

On the Title Page under "Foreign Patent Documents" add

-- 57-190567    Japan --.

Signed and Sealed this

Fourth Day of October, 1988

Attest:

DONALD J. QUIGG

Attesting Officer

Commissioner of Patents and Trademarks